United States Patent [19]

Sengupta

[11] Patent Number: 4,680,382

[45] Date of Patent: Jul. 14, 1987

[54] ANALOGUES OF ACTINOMYCIN D

[75] Inventor: Sisir K. Sengupta, Needham, Mass.

[73] Assignee: Trustees of Boston University, Boston, Mass.

[21] Appl. No.: 825,290

[22] Filed: Feb. 3, 1986

[51] Int. Cl.$^4$ .............................................. C07K 5/12
[52] U.S. Cl. ................................................ 530/317
[58] Field of Search ....................................... 530/317

[56] References Cited

PUBLICATIONS

Journal of Medicinal Chemistry, vol. 28, No. 5 (1985) 620–628.

*Primary Examiner*—Delbert R. Phillips
*Attorney, Agent, or Firm*—Paul J. Cook

[57] ABSTRACT

Analogues of actinomycin D are provided which are effective in the therapeutic treatment of cancer. The analogues have the formulas:

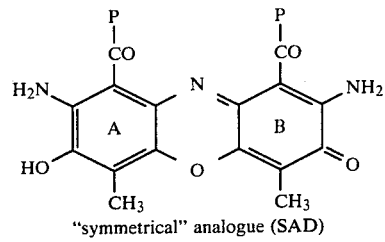

"symmetrical" analogue (SAD)

or

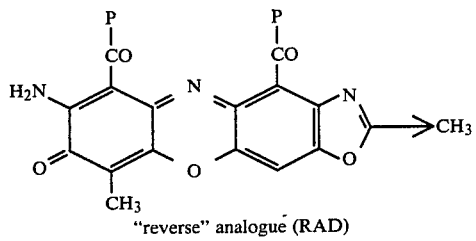

"reverse" analogue (RAD)

wherein P = Thr—D-Val—Pro—Sar—MeVal
                └──────O──────┘

2 Claims, No Drawings

ANALOGUES OF ACTINOMYCIN D

BACKGROUND OF THE INVENTION

This invention relates to new analogues of actinomycin D and to a method of preparing them.

Actinomycin D (AMD) is disclosed in German patent No. 1,172,680 and is a chromopeptide antibiotic whose potent activity in several tumors, including Wilm's tumor, gestational choriocarcinoma and Kaposi's sarcoma, has been reported. It has the formula:

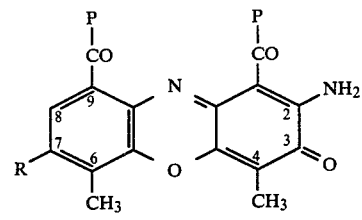

wherein P is Thr—D-Val—Pro—Sar—MeVal
             └─────── O ───────┘ and R is hydrogen. AMD at submicromolar concentrations strongly inhibits DNA-dependent RNA synthesis and, to a lesser extent, DNA synthesis. Its interaction with DNA has been extensively studied, and the details of the mechanism of binding to DNA has been proposed, E. Reich, Cancer Res., 23, 1428 (1963), W. Muller and D. M. Crothers, J. Mol. Biol., 35, 251 (1968), and H. M. Sobell and S. C. Jain, J. Mol. Biol., 68, 21 (1972). It has been assumed that the cytotoxicity of AMD is due to its inhibition of RNA polymerase following the intercalative binding to DNA. It is quite possible, however, that the distortions in helical DNA resulting from the strong noncovalent association with AMD may not be solely responsible for the observed biological effects. For example, Nakazawa et al, J. Org. Chem., 46, 1493 (1981) suggest that an intermediate free-radical form of AMD may be the active form that causes DNA damage and cell death.

Furthermore, the proximal mechanism of biochemical action of AMD, which is evident from the inhibition of RNA synthesis, may not be the principal mechanism of selective cytotoxicity of the agent at the pharmacological level. For it is known that AMD is far more cytotoxic in those proliferating cells in which it inhibits DNA synthesis than in those of liver, kidney, muscle, etc., that are nonproliferating but are heavily dependent upon RNA synthesis for protein renewal.

Another pharmacological behavior of AMD is that it is not metabolized in vivo. Absence of metabolic conversion or detoxification of AMD leads to its accumulation in the cell nuclei of the host organs and causes cumulative toxicity. This acute cumulative toxicity limits the wide clinical application of AMD.

Accordingly, it would be desirable to synthesize new pharmacologically active analogues of AMD having increased drug efficacy. To achieve this, it would be desirable to increase the drug potency, by enhancing drug activity in the tumor cells and decrease toxicity to the host.

SUMMARY OF THE INVENTION

In describing this invention, the following notation as relates to the products of this invention is shown by Formula 4 and Formula 7.

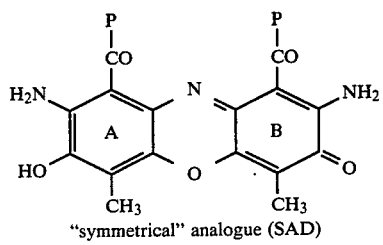

"symmetrical" analogue (SAD)

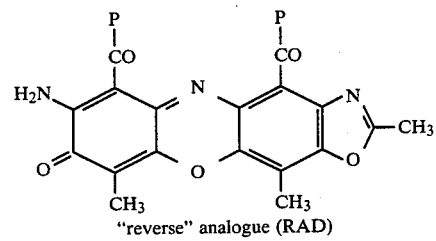

"reverse" analogue (RAD)

wherein (a) P = —Thr—D-Val—Pro—Sar—MeVal, ppl
         └─────── O ───────┘
(pentapeptidolactone)

(b) P = —N(C₂H₅)₂, dea (diethylamine).

The compounds 4a and 7a are novel compounds and are active and toxic against human cancer cells.

The compounds of this invention as well as closely related compounds to be tested for anticancer activity are produced by the schematic process shown in Chart I.

CHART I

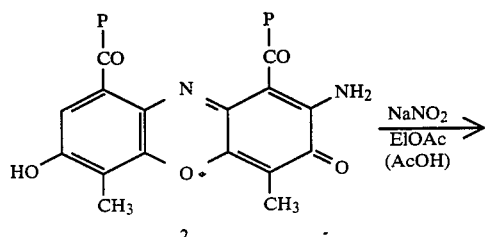

-continued
CHART I

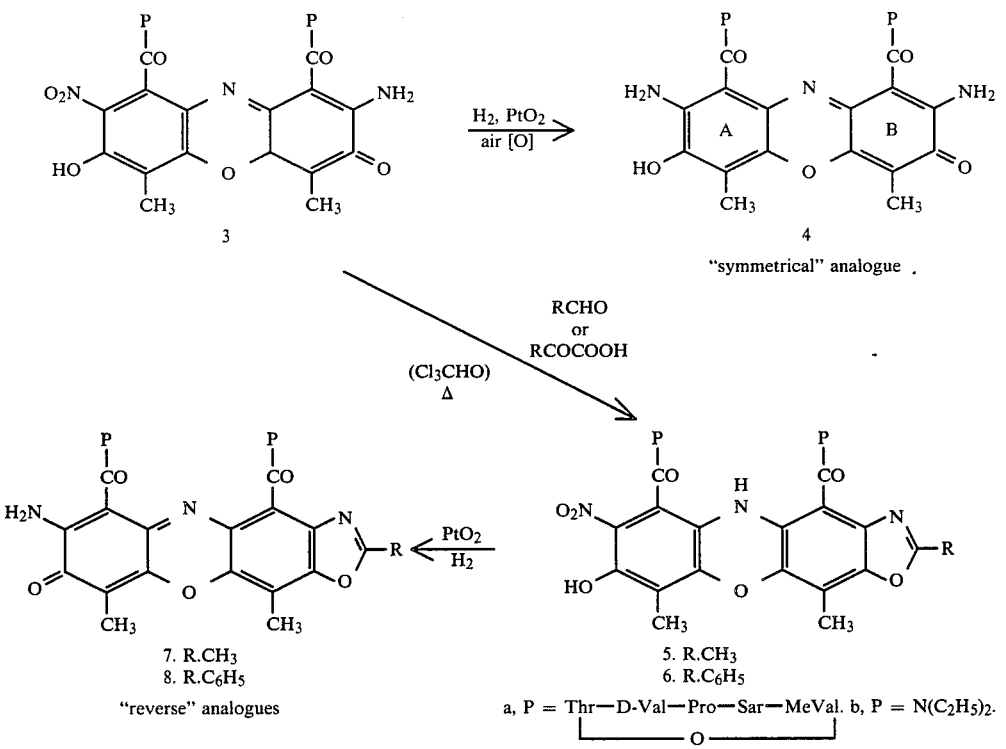

4 "symmetrical" analogue

7. R.CH₃
8. R.C₆H₅

"reverse" analogues

5. R.CH₃
6. R.C₆H₅ a, P = Thr—D-Val—Pro—Sar—MeVal. b, P = N(C₂H₅)₂.
└─────────── O ───────────┘

The model analogues 1b–8b retain the chromophores, but not the pentapeptide lactone (P) groups; instead, they carry diethylamide functions (Chart I) at the sites of the peptide lactones. The "reverse" AMD analogues 7a and 8a carry the entire chromophore of AMD but differ from AMD in their three-dimensional structure. The oxazole ring in these analogues was formed at the expense of the original 2-amino and 3-oxo functions located on the B ring of AMD; these functions are regenerated on the A ring. Consequently, the relative steric relationship of the newly generated functions and especially that of the 2-amino function in relation to the hydrogen bonded P groups is different from the one in AMD. The two ($\alpha$, $\beta$) peptide (P) lactones in actinomycin D (1a) are reported to be hydrogen bonded by interannular bonds, thereby giving a relatively rigid geometry of the one P vs. the other. In addition, the $\beta$-peptide is hydrogen bonded further to the 2-amino function of AMD and the $\alpha$-peptide is not. As a result of this and other nonsymmetrical hydrogen bondings of the peptide (P) and the chromophoric functions (2-amino and N-10), the original peptide conformations of AMD would appear to be reversed in the "reverse" analogues (imagine rotating the "reverse" analogues 180° around their $N^5$-$O^{10}$ axis).

Actinomycin and related tetracyclic analogues, designed as better substrates for microsomal enzymes and for generation of free-radical species and which presumably would make them more specific for the hypoxic tumor cells, e.g., melanoma and colon carcinoma are of interest. Typical of these analogues, actinomycin D oxazolyls "AMD-OZL" 9a and 10a and "reverse" AMD analogues 7a and 8a are shown (Chart I). They retain the cyclic pentapeptides of AMD; however, they also feature an extra oxazole ring attached to the original phenoxazine chromophore of AMD.

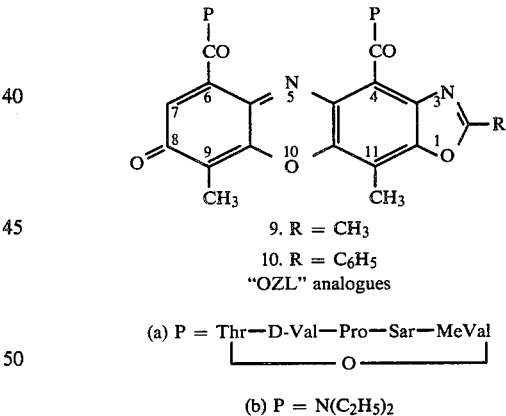

9. R = CH₃
10. R = C₆H₅
"OZL" analogues (a) P = Thr—D-Val—Pro—Sar—MeVal
└─────────── O ───────────┘

(b) P = N(C₂H₅)₂

In preparing the compounds of this invention, 7-hydroxyactinomycin D (2a) is nitrated at the 8-position with aqueous sodium nitrite in ethyl acetate medium at 0° C. to give 3a in a respectable yield (75–80%). The 2-amino and 3-oxo functions in compound 3a are transformed into an oxazole ring following the procedure described by us. Either pyruvic acid or benzoyl formic acid gives the respective oxazoles. However, in analogue 3a (P=peptide lactones), the condensation reaction is accomplished only with a prior treatment of 3a with chloral hydrate, which is known to disengage the hydrogen bonds between the 2-amino group and the peptide lactones. The yields of the 7-nitro-8-hydroxyoxazoles 5a and 6a are in the order of 70–80%. In the model analogues (3b, P=NEt₂), the reaction proceeds without aid of chloral. Alternatively, benzaldehyde can be used instead of benzoylformic acid to synthesize 6a. Catalytic reduction of the 7-nitro group in 5a and 6a to the 7-amino group produces intermediate 7-amino-8-hydroxy derivatives, which are readily oxidized in air, as before, to the red amino o-quinone derivatives. The yields of the "reverse" analogues 7a and 8a are almost quantitative. The "symmetrical" analogue 4a is obtained via a similar catalytic reduction of 3a (Chart I).

The synthesis of 5a–8a is accomplished following the procedures for 5b–8b which are reported.

In physicochemical properties, the "reverse" analogues of actinomycin D are closer to AMD than to the AMD-OZL analogues. The UV-visible absorption spectra for "reverse" methyl analogue 7a in chloroform show the characteristic double absorption maxima of the amino o-quinone of phenoxazine, e.g., $\lambda_{max}$(CHCl$_3$) 450 and 430 nm, compared to AMD, $\lambda_{max}$(CHCl$_3$) 442 and 424 nm. Similarily, the "reverse" phenyl analogue 8a has a double maxima at 458 and 445 nm. On the other hand, the AMD-OZL analogues show lone long-wavelength maximum at 498 nm (for phenyl-OZL, 6a) and 510 nm (for methyl-OZL, 5a). The long-wavelength absorption maximum of the "symmetrical" analogue 4a is at 473 nm.

TABLE I

Comparison of NMR Chemical Shifts ($\delta$ Values) of Protons in "Symmetrical" AMD, 2-Phenyl-AMD—OZL, (10a), "Reverse" Phenyl AMD Analogue (8a) and AMD[a]

| proton | AMD | "symmetrical" analogue 4a | proton | "reverse" phenyl 8a | AMD—OZL (2-phenyl) 10a |
|---|---|---|---|---|---|
| H$_7$[b] | 7.37 | | H$_8$ | | |
| H$_8$[b] | 7.64 | | H$_7$ | | 6.75 |
| 4-Me[b] | 2.56 | 2.32 | 11-Me | 2.64 | 2.67 |
| 6-Me[b] | 2.34 | 2.32 | 9-Me | 2.36 | 2.27 |
| D-Val NH ($\alpha$ or $\beta$) | 8.09 | 8.09 | | 8.07 | 8.55 |
| D-Val NH ($\alpha$ or $\beta$) | 7.94 | 7.93 | | 7.92 | 8.48 |
| Thr NH ($\alpha$ or $\beta$) | 7.82 | 7.82 | | 7.81 | 6.82 |
| Thr NH ($\alpha$ or $\beta$) | 7.20 | 7.21 | | 7.18 | 6.73 |

[a]In CDCl$_3$ solvent, 100 MHz (JEOL FQ-90 MHZ). Chemical shifts in parts per million ($\delta$) to low field from internal Me$_4$Si.
[b]H$_7$, H$_8$, 6-Me and 4-Me in AMD = H$_8$, H$_7$, 11-Me and 9-Me in "reverse" and AMD—OZL.

The NMR chemical shifts (Table I) and specific rotation data suggest that the molecular conformations of AMD and the "reverse" and "symmetrical" analogues are similar and are different from those in AMD-OZL analogues. In AMD (1a), the peptide lactones are held in a special conformation by the interannular hydrogen bonds between the NH of D-valine ($\alpha,\beta$) and the carbonyl of D-valine ($\alpha,\beta$), respectively. Moreover, one of the protons in the 2-amino group in AMD is shown to be hydrogen bonded, linking the $\beta$-pentapeptide lactone threonine NH and the chromophore N-10. The conformations of the peptide lactones in AMD-OZL analogues 9a and 10a are altered due to the lack of these functions. Also, the A ring in AMD-OZL analogues 9a and 10a is in the form of quinone imine as is the B ring in AMD. This is more so for the "reverse" analogues where the quinoid ring methyls and the benzenoid ring methyls have almost identical chemical shift values of the AMD ring methyls (Table I). However, in spite of a closer similarity between the two-dimensional structures of AMD and the "symmetrical" AMD analogue, there is some difference in the UV absorption and in NMR properties. The NMR chemical shifts ($\delta$) of the two ring methyls and also of the two ring amino hydrogens in the "symmetrical" analogue are the same; this is due to a rapid tautomerization between the quinoid and the benzenoid rings, A and B.

The peptide conformations of AMD and of the previously reported AMD-OZL analogue 9a are somewhat different; in contrast, there is a striking similarity in these features in AMD and the "reverse" analogues which are also evident from the chemical shift ($\delta$) values of the D-valine and threonine NH (Table I). Also, there appears to be a relationship between the specific rotation values ($[\alpha]^{20}$nm) and ellipticity values ($[\theta]$) in the circular dichroic spectra of AMD and analogues; that these values can serve as indicators of the peptide conformations has been established. The specific rotation values of AMD and "symmetrical" and "reverse" analogues are practically the same. In short, conformation of peptides in AMD is noticeably different from that of "AMD-OZL" analogues.

The "reverse" analogues bind to calf-thymus DNA, but the spectrophotometrically determined binding (K$_{app}$ and B$_{app}$, equilibrium binding values) constants are found to be lower than those of AMD. The binding is also measured by thermal denaturation of DNA. The results of these studies suggest that there is a pronounced effect on the DNA-binding properties by the amino group at C-7 of 7a and 8a; the "AMD-OZL" analogues do not carry this amino group and fail to bind to DNA ($\Delta T_m = 0°–1°$ C.).

The equilibrium binding constants (K$_{app}$ and B$_{app}$) of the "reverse" methyl 7a and the "reverse" phenyl 8a were determined from the Scatchard plots of binding isotherms; the Scatchard plots are produced according to the previously described methods using calf-thymus DNA [Sengupta et al, Biochem. Biophys. Acta 521, 89 (1978)]. The K$_{app}$ values are $2.5 \times 10^6$ and $2.3 \times 10^6 M^{-1}$, respectively; corresponding B$_{app}$ values are 0.038 and 0.036. DNA melting temperature showed $\Delta T_m$ values $5.5 \pm 0.3$ for 7a and $6.7 \pm 0.2$ for 8a, exhibiting DNA binding. But, these "reverse" analogues associate with DNA less strongly; their frequency of binding is also lower compared to that of AMD. However, the "reverse" analogues fail to cause any measurable change in the ratio of the intrinsic viscosity ($\gamma$) of DNA with the increasing ratios of [ligand]/DNA base pair (r), even when low molecular weight DNAs ($0.5 \times 10^5$ to $1.0 \times 10^5$) were employed. Under identical conditions, AMD showed a steady rise in the value of $\gamma$ with increasing r values. These viscometric experiments establish the fact that these "reverse" analogues, in contrast to AMD, do not intercalate into DNA.

The "symmetrical" analogue 4a was found to associate with DNA more strongly than AMD ($\Delta T_m = 7.9 \pm 0.2$ and K$_{app}$ and B$_{app}$ values $6.3 \times 10^7 M^{-1}$ and 1.3, respectively, compared to the corresponding values for AMD ($\Delta T_m = 7.1 \pm 0.15$ and K$_{app} = 2.3 \times 10^7 M^{-1}$ and B$_{app} = 0.108$). Like the "reverse" analogues, the "symmetrical" analogue 4a demonstrates lack of intercalative binding by viscometry. There is an apparent dichotomy in the absence of intercalative binding and the evidence of a strong binding to DNA by the "symmetrical" analogue. This molecule demonstrates rapid equilibration in solution. In this respect, this analogue is unique and is distinctly different from AMD and its various other analogues or even other tricyclic intercalative agents that we have known so far.

A method of using tumor cell sonicates was developed to study the metabolism of the analogues of AMD. By use of sonicated cells, the dilution effects that would occur if flasks of cultured cells were used are avoided. Although the cells are disrupted by this method, their enzyme systems appear to remain active. Large numbers of tumor cells (P388 murine leukemia) were sonicated in Earle's balanced salt solution (EBSS) and were incubated with tritiated AMD and its analogues 7a and 9a (Table II) for 16 hr. In another experiment, the analogues were treated with rat hepatic microsomes at 37° C. for 6 hr in the presence of a NADPH-generating system. The metabolic products were isolated and identified with the following results (Table II). The analogues were found to be metabolized to major known products with the loss of the oxazole ring from both "reverse" and "AMD-OZL". The "symmetrical" analogue 4a was found to be formed from the "reverse" 7a analogue; the AMD-OZL analogue 9a was metabolized to 7-hydroxy-AMD (2a). In the microsomes, the major metabolites were in unconjugated forms; in the tumor cell homogenates, the major identified metabolites were glucuronide and sulfate conjugated forms. It should be pointed out that in these metabolic experiments, the identification of these glucuronide and/or sulfate conjugates was made only on the basis of the disappearance of the peaks from the HPLC chromatograms upon treatment with deconjugating enzymes glucarase. In each case, large amounts of unmetabolized materials were also isolated suggesting slow metabolism of the substrates in these experimental systems.

TABLE II

Percent Metabolite Isolated from Incubation Mixture Containing Tumor Cell Homogenate (T) or Rat Liver Microsomes (M)

| products isolated from the mixture | drugs examined | | |
|---|---|---|---|
| | AMD, % | "AMD—OZL" CH$_3$ 9a, % | "reverse" CH$_3$ 7a % |
| unconverted | 100(T,M) | 20(T), 38.5(M) | 40(T), 21(M) |
| 7-hydroxy-AMD (2a), 5.1 min (I), 12.8 min (II)[a] | | 8.5(T), 40.5(M) | |
| "symmetrical" AMD (4a) 7.7 min (I), 20.0 min (II)[a] | | | 15.5(T), 62.5(M) |
| 2a glucuronide and/or sulfate, 12.0, 13.0 min (II); 19.0, 22.0 min (III)[a] | | 12.2(T), nil(M) | |
| 4a glucuronide and/or sulfate, 8.0, 10.5 min (II); 16.0, 21.0 min (III)[a] | | | 17.5(T), nil(M) |
| protein conjugates | | 5.5(T), 9.5(M) | 5.5(T), 3.5(M) |
| "tissue" bound | | 7.5(T), 5.5(M) | 8.8(T), 3.7(M) |
| unidentified metabolite | | 46.3(T), 6(M) | 12.7(T), 8.5(M) |

[a] HPLC $t_R$ in minutes (systems used I, II and III, see Example)

Some protein adducts and tissue-bound products were also isolated. These adducts were probably formed by drugs or their metabolites binding covalently to proteins; they were not deconjugated from the protein fraction on Sephacryl gel filtration in denaturing 6M guanidine hydrochloride medium, pH 5.0, which is known to dissociate noncovalently bound materials from protein.

Actinomycin D did not form any detectable metabolite or conjugate, confirming that AMD is not metabolized in these systems. Formation of covalently bound protein metabolite adducts indicates that reactive metabolites, possibly free-radical intermediates of drugs, were formed during the formation of these adducts.

The phenoxazinone ring system in AMD and some of its analogues are capable of enzymatic single-electron reduction. A free-radical intermediate is formed, which subsequently transfers an electron to oxygen, yielding a superoxide $O_2^-$. The activation to free-radical intermediates is known to be mediated by microsomal enzymes which require cofactors, one of which is NADPH. In this process, NADPH is oxidized to $NADP^+$; and an electron is transferred to quinone imine, forming the quinone imine radical. This ion radical can generate superoxide radicals by transferring the electron to oxygen. When these superoxides are allowed to react with epinephrine, they produce another chromophore, N-methylindolequinone, commonly known as adrenochrome. The progress of this reaction, therefore, can be monitored spectrophotometrically by the rate of oxidation of NADPH to $NADPH^+$ at 340 nm and also by the absorbance of adrenochrome at 480 nm. The relative efficiencies of induction of the above processes by AMD and its analogues 2a, 4a, 7a and 9a and the corresponding model analogues 1b, 2b, 4b, 7b and 9b were measured at 37° C. in the presence of purified phenobarbital induced microsomes with the results shown in Table IV. The data show that actinomycin D induced the stimulation of oxidation of NADPH at 9.9% over the basal level, i.e., when no drug was used. 7-Hydroxy-AMD (2a) promoted the rate to 228% and the "symmetrical" analogue 4a did so by 606%. The "reverse" analogue 7a stimulated the process by 134% and the AMD-OZL analogue 9a expdeited it by 110%. The corresponding model derivatives (b series) did not have any measurable effect.

TABLE IV

Stimulation of NADPH Oxidation and Adrenochrome Formation by Actinomycin D and Its Analogues by Rat Hepatic Microsomal Incubations

| compd | NADPH oxid,[a] nmol min$^{-1}$ (mg of protein)$^{-1}$ | SOD,[b] 5 μg/mL | adrenochrome formation,[a] nmol min$^{-1}$ (mg of protein)$^{-1}$ |
|---|---|---|---|
| | 9.11 ± 0.30 | — | 2.11 ± 0.11 |
| AMD (1a) | 10.01 ± 0.90 (9.9) | — | 2.29 ± 0.33 (8.5) |
| | | + | inhibited |
| 7-OH—AMD (2a) | 29.9 ± 1.91 (228) | — | 7.29 ± 0.79 (245) |
| | | + | inhibited |
| 4a | 64.3 ± 2.11 (606) | — | 19.3 ± 1.04 (815) |
| | | + | inhibited |
| 7a | 21.3 ± 1.93 (134) | — | 6.04 ± 0.19 (186) |
| | | + | inhibited |
| 9a | 19.1 ± 1.70 (110) | — | 4.36 ± 0.21 (106) |
| | | + | inhibited |
| 1b, 2b, 4b, 7b and 9b | 8.9 ± 0.90 (−2) | — | 2.13 ± 0.19 (+1) |

[a] The percentage stimulation = [(drug-stimulated rate basal rate)/basal rate] × 100 and is shown in parentheses. NADPH oxidation was measured at 340 nm and adrenochrome formation was measured at 480 nm; the values are the average ± standard errors of triplicate analyses.
[b] SOD, superoxide dismutase from bovine liver, 3000 units/mg of protein.

Some analogues show high absorbance values at 480 nm; therefore, no more than 100 μM of drug was used during assay of adrenochrome formation at this wavelength. AMD and its analogues showed stimulation of adrenochrome formation, which is an indicator of generation of superoxides. The rate of stimulation by AMD was found to be 8.5% over the basal level (see Table IV), by 7-hydroxy-AMD 245%, by the "symmetrical" analogue 4a 815%; by the "reverse" analogue (7a) 186% and by the AMD-OZL analogue 9a 106%. The model derivatives 1b-9b were ineffective, as in the preceding experiment. Furthermore, addition of 5 μg/mL of SOD in these experiments completely inhibited formation of adrenochrome, suggesting that $O_2^-$ was indeed responsible for this adrenochrome formation.

Experiments for inhibition of nucleic acid synthesis in tumor cells in vitro were carried out with P388 tumor cells, details of which were reported by Sengupta et al, J. Med. Chem., 18, 1175 (1975). AMD is known to be more effective in inhibiting RNA synthesis than DNA synthesis in P388 and L1210 leukemia cells in culture. Table III shown that the $IC_{50}$ DNA value for AMD is 22 times the $IC_{50}$ RNA value, indicating the strong preference shown by AMD for blocking RNA synthesis in these cells. 7-Hydroxy-AMD inhibits RNA synthesis with less selectivity and is also less potent than AMD. AMD-OZLs inhibit either process with equal activity and with the potency of its metabolite 7-hydroxy-AMD. Whereas the "reverse" analogues appear to mimic AMD activity, their metabolite "symmetrical" analogue 4a is different and is about equally active in inhibiting both the processes transcription and replication in cells and is about as potent as its precursor "reverse" analogues and AMD in inhibiting replication.

TABLE III

Inhibition of Nucleic Acid Synthesis by AMD—OZL and "Reverse" and "Symmetrical" AMD Analogues

| compd | in vitro (CCRF—CEM)[a] $ID_{50}$, nM | $IC_{50}$ values, μM RNA[b] synth | $IC_{50}$ values, μM DNA[c] synth | $IC_{50}$ DNA/ $IC_{50}$ RNA |
|---|---|---|---|---|
| AMD | 50 | 0.05 | 1.12 | 22.40 |
| 7-hydroxy-AMD (2a) | 1000 | 5.1 | 5.1 | 1.00 |
| AMD—OZL—$C_6H_5$ (10a) | 500 | 3.2 | 5.7 | 1.78 |
| "reverse" $CH_3$ 7a | 110 | 0.09 | 1.01 | 11.22 |
| "reverse" $C_6H_5$ 8a | 30 | 0.07 | 0.80 | 11.43 |
| "symmetrical" analogue (4a) | 30 | 1.15 | 1.11 | 0.97 |

[a]Human lymphoblastic leukemic cells.
[b]$IC_{50}$ (RNA) = concentration of inhibitor in μM required to cause 50% reduction (in 1 hr) in 2-[$^{14}$C]uridine incorporation into acid precipitable material with use of P388 cells.
[c]$IC_{50}$ (DNA) = concentration of inhibitor in μM required to cause 50% reduction (in 1 hr) in methyl[$^3$H]thymidine incorporation into acid precipitable material with use of P388 cells.

A free-radical intermediate with broad resonance peaks was detected by EPR when anaerobic solutions of NADPH, actinomycin D (1a), and potassium phosphate buffer were reacted with liver microsomes. Free-radical intermediates were also detected when the "symmetrical" analogue 4a and "reverse" analogue 7a were treated with microsomes under identical conditions. No free-radical intermediates were detected in the absence of enzyme or substrates. However, no free-radical intermediates were detectable by reductive activation of the actinomycin model derivatives, e.g., "reverse" 7b or "symmetrical" 4b under similar conditions.

The analogues were tested for their antitumor activities in P388 lymphocytic leukemia in male BDF$_1$ mice. The tumor was implanted intraperitoneally (ip) with $10^6$ cells. The drugs were also administered ip once daily on days 1, 5 and 9, beginning 1 day after tumor transplantation. Analogues were tested over a range of doses, but only the optimal nontoxic doses are listed. In this system, in which AMD is known to be very effective, the "reverse" analogues and the "symmetrical" 4a are found to be about threefold more effective than AMD in respect of % ILS values and also in producing long-term survivors. The analogues 9a and 10a are less effective than the above analogues, but they are better effective than AMD or 7-hydroxy-AMD and produce more longer living animals during this treatment (Table V).

TABLE V

In Vivo Antitumor Activity of AMD, AMD—OZL, and "Reverse" and "Symmetrical" Analogues against P388 Leukemia[a]

| compd | optimal dose, μg/kg per inj | MST (range), days | % ILS (surv) |
|---|---|---|---|
| no drug (control) | | 11.0 (9–12) | |
| actinomycin D (1a) | 300.0 | 26.0 (16–37) | 136 (1/8) |
| 7-hydroxy-AMD (2a) | 1200.0 | 26.0 (19–39) | 136 (0/8) |
| AMD—OZL, —$CH_3$ (9a) | 1200.0 | 29.0 (19–58) | 164 (0/0) |
| AMD—OZL, —$C_6H_5$ (10a) | 1000.0 | 31.5 (29–57) | 186 (2/8) |
| "reverse" $CH_3$ 7a | 450.0 | 42.5 (39–43) | 277 (3/8) |
| "reverse" $C_6H_5$ 8a | 375.0 | 52.0 (49–58) | 382 (4/8) |
| "symmetrical" AMD (4a) | 600.0 | 52.0 (48–55) | 382 (4/8) |

[a]$10^6$ P388 cells implanted ip on day 0 into groups of eight BDF$_1$ male mice. Drugs administered ip. MST (range), median survival time in days (range of individual animal deaths); % ILS, percent increase in life span, calculated 100(T/C − 1), where T and C are median survival times of treated and control animals; surv, number of surviving mice/total mice, at 60 days.

By use of a similar protocol with B$_{16}$ melanoma, the "reverse" and the "symmetrical" analogues were again found to be superior antitumor agents (Table VI). AMD-OZL analogues 9a and 10a were about as active as AMD and 7-hydroxy-AMD. The potencies of these analogues are reduced in comparison to that of AMD; their optimal doses were higher than that of AMD.

TABLE VI

In Vivo Antitumor Activity of AMD and AMD Analogues against B$_{16}$ Melanoma[a] (Treatment: Days 1, 5, 9)

| compd | optimal dose, μg/kg per inj | MST[b] (range) | % ILS (surv)[c] |
|---|---|---|---|
| no drug (control) | | 29 (20–48) | |
| actinomycin D (1a) | 250 | 43 (36–54) | 48 (2/9) |
| 7-hydroxy-AMD (2a) | 1200 | 44 (39–53) | 52 (1/9) |
| AMD—OZL, —$CH_3$ (9a) | 750 | 45 (32–55) | 55 (1/9) |
| AMD—OZL, —$C_6H_5$ (10a) | 900 | 45 (33–56) | 55 (2/9) |
| "reverse" $CH_3$ 7a | 300 | 55 (33–57) | 90 (3/9) |
| "reverse" $C_6H_5$ 8a | 300 | 59 (53–59) | 103 (5/9) |
| "symmetrical" AMD (4a) | 300 | 57 (33–61) | 96 (4/9) |

[a]0.2 mL of 1:5 (weight/volume) brei of B$_{16}$ melanoma implanted ip on day 0 in groups of nine BDF$_1$ mice. Drugs administered ip.
[b]MST (range) median survival time in days (range of individual animal deaths).
[c]% ILS (surv), percent increase in life-span (survivors on day 65/total injected).

The most active analogue of each type, e.g., AMD-OZL 10a, "reverse" analogue 8a and "symmetrical" analogue 4a, was tested against P388/ADR murine leukemia tumor cell line following the standard protocol (Table VII), Johnson et al, Cancer Treat. Rep. 62, 1535 (1978). This tumor line is known to be resistant to intercalating agents including actinomycin D and adriamycin; however, the tumor is highly sensitive to mitomycin C, which is believed to act via activation of its quinone chromophore to a free-radical form. The "reverse" and the "symmetrical" analogues show high levels of activity, and we have found that these analogues do not intercalate into DNA. The activities of the analogues 4a and 8a were found to be intermediate between those of mitomycin C and actinomycin D. The active analogues were also found to be active over a broader dose range compared to AMD in this and also in actinomycin-sensitive P388/S and B16 tumor lines.

TABLE VII

Effect of AMD, AMD—OZL (10a) and "Reverse" (8a) and "Symmetrical" (4a) on BDF$_1$ Mice with P388/Adriamycin-Resistant Leukemia[a]

| drug | dose range, mg/kg per inj, ip | P388/S optimal dose | | P388/ADR optimal dose | |
|---|---|---|---|---|---|
| | | mg/kg | % ILS | mg/kg | % ILS |
| adriamycin | 2.5–4.5 | 3.0 | 97 (1/8) | 3.5 | 33 |
| actinomycin D (AMD) | 0.075–2.5 | 0.25 | 132 (1/8) | 0.25 | 22 |
| "reverse"—C$_6$H$_5$ 8a | 0.10–0.8 | 0.35 | 382 (4/8) | 0.6 | 132 (1/8) |
| AMD—OZL—C$_6$H$_5$ (10a) | 0.20–1.2 | 1.0 | 186 (2/8) | 1.2 | 88 |
| "symmetrical" AMD (4a) | 0.3–1.8 | 0.6 | 382 (4/8) | 1.2 | 176 (3/8) |
| mitomycin C | 1.0–5.0 | 3.0 | 136 (1/8) | 3.0 | 400 (5/8) |

[a]Male BDF$_1$ mice inoculated ip: 10$^6$ cells inoculum, day 0. Drugs administered in 10% dimethyl sulfoxide-saline on days 1, 5 and 9. % ILS = percent increase in life span. Fractions in parentheses = tumor-free survivors/total on day 60. P388/S (adriamycin sensitive) and P388/ADR (adriamycin resistant) tumors were evaluated in the same experiment with the agent listed.

These analogues were also tested in tumor-free BDF$_1$ male mice for determination of their MTD values (Table VIII). The animals (18–22 g) were given a broad range of doses of drugs in 5% dimethyl sulfoxide-saline on days 1, 5 and 9. Drugs were administered ip and the maximum tolerated doses of agents which caused death in only 10% of the tested animals in 21 days (i.e., LD$_{10}$) were recorded as MTD. Data in Table VIII show that the MTD values of all the analogues except that of 7-hydroxy-AMD are about seven- to tenfold of the MTD dose of AMD; for 7-hydroxy-AMD, it is higher and is about 14-fold of the MTD value of AMD. However, the MED values of 7-hydroxy-AMD and its precursor AMD-OZL 10a are high and are seven to tenfold of the MED values of 4a and 8a. On the basis of these MED values, the therapeutic indices of 8a and 4a are 70 and 96. The therapeutic index of 2a is 13, of 10a 10, and of AMD only 4.

The analogues were tested for their cytotoxicity against tumor cells (time, 48 hr). The in vitro cytotoxicity (ID$_{50}$, CCRF-CEM) value of AMD is 50 nM (Table III), of 7a 110 nM and of 8a and of 4a 30 nM. Like the "reverse" analogue, the "symmetrical" analogue demonstrates substantial reduction of toxicity in vivo in spite of extremely high in vitro cytotoxicity. This may be associated with the initial microsomal transformation of the "reverse" analogues to "symmetrical" analogue and/or other alternate bioactive forms (e.g., free-radicals, O$_2^-$), followed by deactivation via formation of conjugates and facile elimination of these from the host. The "reverse" analogues show reduced toxicity in vivo and also the tritiated "reverse" 7a is metabolized in vitro.

TABLE VIII

Comparison of AMD with Chromophore-Substituted and Tetracyclic Chromophoric Analogues of AMD vs. P388 Leukemia[a]

| drug | MED[b] | MTD[c] | therapeutic index MTD/MED |
|---|---|---|---|
| AMD (1a) | 0.0625 | 0.25 | 4 |
| 7-OH—AMD (2a) | 0.275 | 3.50 | 13 |
| AMD—OZL (10a) | 0.20 | 2.0 | 10 |
| "reverse" C$_6$H$_5$ 8a | 0.03 | 1.80 | 60 |
| "symmetrical" AMD (4a) | 0.025 | 2.40 | 96 |

[a]Drugs administered ip once on days 1, 5 and 9 starting 1 day after tumor implantation. Determinations were made from analysis of plotted log-dose response data.
[b]MED (minimum effective dose) is the dose (milligram/kilogram) providing an increase in life span of 45% over control in P388 tumor bearing mice.
[c]MTD (maximum tolerated dose) is the lethal dose (milligram/kilogram) for 10% normal BDF$_1$ male mice (18–22 g); animals observed for deaths during 21 days (LD$_{10}$ = 21 days). Values were calculated from a plot of log-dose vs. percent mortality.

These experiments establish the "symmetrical" analogue as the most active agent; it is a very efficient agent in stimulating radical formation. 7-Hydroxy-AMD, which is the closest in structure to this analogue 4a, is the next best inducer of radicals; like the "symmetrical" analogue, 7-hydroxy-AMD is also in an equilibrium of its two isomeric forms in solution. The biological activity of the "reverse" analogue 7a is intermediate between those of 2a and the "symmetrical" analogue. AMD is least active in all these systems. The peptide-free analogues 1b-9b are ineffective. These results strongly suggest that the peptide moieties play an important role when the analogues participate in the transport of electrons from the enzymes to oxygen with consequent biological activity. Also, those chromophores which have extended resonating structures act as better intermediaries in the radical-forming reactions.

There is a noticeable similarity in the metabolism of 7a and 9a. Although a large portion of the metabolites are not identified, the pattern of metabolic conversion for each analogue is practically the same. There are some differences in the quantities of the metabolites obtained from these analogues. AMD-OZL analogues do not bind to DNA and their peptide conformation is somewhat different from the "reverse" analogues and also from AMD. It probably indicates that this small alteration in the peptide confromation does not eliminate the analogues' ability to react with digestive enzymes and to undergo metabolic conversions.

In biological systems, actinomycin and its quinone imine chromophoric analogues can be activated like other quinone xenobiotics to free-radical intermediates. The formation of these ion radicals is found to be facilitated in modified actinomycin analogues. These modified actinomycins are found to act as improved antitumor agents against leukemia and melanoma in mice. DNA intercalation and radical formation are not apparently related because these analogues do not intercalate into DNA. Extended resonance conjugation in quinone imine chromophore in active analogues enhances the sensitivity for radical formation, and other structural features like the conformation of the peptides determine the specificity for interaction with activating enzymes. The analogues which are metabolized in cell homogenates and in microsomes show reduced toxicity in vivo, suggesting that metabolic conversions of these agents in vivo might play an important role in improving the therapeutic index values.

The following example illustrates the present invention and is not intended to limit the same.

EXAMPLE I

Melting points are determined on a Thomas-Hoover melting point apparatus at a heating rate of 2° C./min. Thin-layer chromatography was performed on silica gel plates (Brinkmann Instrument Inc.). Solvent systems were (A) EtOAc-acetone (4:1), (B) CHCl$_3$-MeOH (9:1) and (C) Cifferri, the organic phase of the mixture EtOAc-MeOH-H$_2$O (20:1:20). High-performance liquid chromatography was carried out on a Varian Model 5020 gradient liquid chromatograph equipped with a CD-111L chromatography data system and fitted with a Varian reversed-phase C$_{18}$ column with the following solvent systems: I, CH$_3$CN-5 mM NH$_4$OAc buffer, pH 6.4 (68:32 isocratic), flow rate 1.5 mL/min; II, 65–95% water-methanol gradient for 70 min, 1 mL/min; III, 10–90% H$_2$O-MeOH gradient for 120 min, 1 mL/min, with UV-visible variable- and fixed-wavelength dual detectors at 254, 440, 470 and 520 nm. IR spectra were obtained on a Perkin-Elmer Model 237 Infra Cord with KBr micropellets or in chloroform solutions. UV-visible spectra were obtained on a Gilford 250 spectrophotometer, which, with the addition of a base-line reference compensator (Analog Multiplexer 5053) and thermoprogrammer, auto four cell programmer and thermoelectric cell holder 2577, were used to obtain thermal denaturation curves. Specific rotation values were determined in chloroform solutions with a Cary 60 spectropolarimeter. NMR spectra were obtained in a JEOL FQ-90 MHz spectrometer equipped with Fourier transform. EPR spectra analyses were recorded in a Varian E-9 EPR spectrometer. All elemental analyses were within ±0.4%.

Synthesis.
2,8-Diamino-1,9-bis(diethylcarbamoyl)-7-hydroxy-4,6-dimethyl-3-H-phenoxazine-3-one (4b)

Compound 3b (500 mg, 1 mmol) was reduced with PtO$_2$ and hydrogen in methanol (50 mL). The reddish purple color of the initial solution was discharged and turned to light green. The solution was diluted with 250 mL of methanol and filtered under nitrogen, which upon slow exposure to air for 18 hr turned deep purple. Evaporation of the solvent gave a dark purple solid, which was crystallized from a mixture of ether-ligroin (30°–60° C.) (1:1) twice to give a dark solid: 395 mg (84%), mp 262°–265°; R$_f$ 0.54 in CHCl$_3$-MeOH (9:1) (solvent B)(R$_f$ 0.22 in solvent A compared to R$_f$ 0.57 of 3b); IR (in KBr) showed absence of the nitro band at 6.5 μm; UV λ$_{max}$ 475 nm (ϵ24100), 287 (inf), 248 (35100); NMR (CDCl$_3$)δ2.26 (s, 6H, 6-CH$_3$ and 4-CH$_3$), 4.16 (s, 4H, 2-NH$_2$ and 8-NH$_2$). The identical (δ) values of 6- and 4-CH$_3$ and 2- and 8-NH$_2$ protons, respectively, indicate a rapid equilibrium between the quinone at C-3 and hydroxyl at C-7, which renders the molecule perfectly symmetrical; in contrast, such equilibrium is not possible in AMD chromophore and consequently AMD has a stable quinone form which is characterized by a double absorption band at 444 and 425 nm. NMR and absorption properties (a lone longwavelength absorption maximum at 475 nm) tend to support that the amino o-quinone form of 4b is not its predominant form in solution. HPLC t$_R$ 10.1 min (CH$_3$CN-5 mM NH$_4$OAc, 62:38, 1.5 mL/min); mass spectrum 469 (M+) Anal. (C$_{25}$H$_{31}$N$_5$O$_5$) C, H, N.

The actinomycin D analogues 3a–8a were synthesized according to the method described above. The physiochemical properties of the various analogues and the yields of their chemical syntheses are as follows:

"Symmetrical" AMD Analogue. 7-Hydroxy-8-amino-actinomycin D (4a): yield 66%; TLC R$_f$ 0.03 (solvent A); UV λ$_{max}$(CHCl$_3$) 473 nm (ϵ19000), 330 (inf), 248 (28140); [α]$^{20}_{644}$−310±15° (c 0.3, CHCl$_3$); HPLC t$_R$ 5.1 min (system I), 12.8 min (system II). Anal. (C$_{62}$H$_{87}$N$_{13}$O$_{17}$.2 H$_2$O) C, H, N.

8-Hydroxy-2,9,11-trimethyl-7-nitro-5H-oxazolo[4,5-b]phenoxazine, 4,6-bis[carbonyl-L-threonyl-D-valyl-L-prolylsarcosyl-L-N-methylvaline-(threonyl hydroxyl)] lactone (5a): yield 85%; TLC R$_f$ 0.56 (solvent A); UV λ$_{max}$(CHCl$_3$) 520 nm (ϵ6300), 345 (9900); [α]$^{20}_{644}$180 −±20° (c 0.2, CHCl$_3$); HPLC t$_R$ 14.7 min (system I). Anal. (C$_{64}$H$_{87}$N$_{13}$O$_{19}$.H$_2$O), C, H, N.

8-Hydroxy-9,11-dimethyl-7-nitro-2-phenyl-5H-oxazolo[4,5-b]phenoxazine 4,6-bis[carbonyl-L-threonyl-D-Valyl-L-prolylsarcosyl-L-N-methylvaline-(threonyl hydorxyl)] lactone (6a): yield 80%; TLC R$_f$ 0.71 (solvent A); UV λ$_{max}$(CHCl$_3$) 498 nm (ϵ 11700), 392 (13300), 301 (20000); [α]$^{20}_{644}$−178±22° (c, 0.2, CHCl$_3$); HPLC t$_R$ 15.7 min (system I), 34.0 min (system II). Anal. (C$_{69}$H$_{89}$N$_{13}$O$_{19}$.H$_2$O), C, H, N.

"Reverse" AMD Analogue (2-Methyl). 7-Amino-2,9,11-trimethyl-8H-8-oxooxazolo [4,5-b]phenoxazine 4,6-bis[carbonyl-L-threonyl-D-valyl-L-prolylsarcosyl-L-N-methylvaline-(threonine hydroxyl)] lactone (7a): yield 91%; TLC R$_f$ 0.20 (solvent A); UV λ$_{max}$(CHCl$_3$) 450 nm (ϵ 28600), 430 (27000) [α]$^{20}_{644}$−280±20° (c, 0.1, CHCl$_3$); HPLC t$_R$ 11.3 min (system I), 28.5 min (system II). Anal. (C$_{64}$H$_{87}$N$_{13}$O$_{17}$.H$_2$O) C, H, N: calcd, 13.53; found, 13.06.

"Reverse" AMD Analogue (2-Phenyl). 7-Amino-9,11-dimethyl-2-phenyl-8H-8-oxooxazolo [4,5-b]phenoxazine 4,6-bis[carbonyl-L-threonyl-D-valyl-L-prolylsarcosyl-L-N-methylvaline(threonine hydroxyl)] lactone (8a): yield 91%; TLC R$_f$ 0.33 (solvent A); UV λ$_{max}$(CHCl$_3$) 458 nm (ϵ 33300), 445 (31000); [α]$^{20}_{644}$−280±20° (c 0.1, CHCl$_3$); HPLC t$_R$ 13.9 min (system I), 31.0 min (system II). Anal. (C$_{69}$H$_{89}$N$_{13}$O$_{17}$.2-H$_2$O) C, H, N.

Metabolism of AMD-OZL (9a) and "Reverse" (7a) Analogues in Tumor Homogenates A large number of P388 cells (10$^8$ cells) were sonicated in Earle's balanced salt solution (EBSS) in ice. Tritiated analogues 7a, 8a and AMD, 0.4 Ci/mmol, were added and the mixtures were incubated at 37° C. for 16 hr. Drugs in EBSS without the addition of the cell sonicates served as controls. The samples were treated with urea to bring the urea concentration to 5M. The procedure helped to free all drugs that associated noncovalently with DNA. After 60 min at room temperature, the samples were centrifuged through Amicon 1053 cone filters (molecular weight cut-off approximately 25000) after adjustment of pH to 5 to facilitate extraction of unconjugated metabolites in organic solvents.

Unconjugated or uncoupled products were first extracted with ethyl acetate (step A) and aliquots of aqueous layers were treated with equal volumes of glucarase (a preparation of β-glucuronidase and sulfatase) or with buffer (control); see following section. The glucuronide and the sulfate derivatives were thus deconjugated and the freed products were extracted in ethyl acetate (step B). A highly sensitive technique for detection of a series of AMD analogues using HPLC was employed; sensitivity of this assay ranges from 50 nmol when UV-visible absorbances are used to 1 pmol when radioactive analogues of appropriate specific activities are used.

The products in the ethyl acetate extracts were analyzed by HPLC using system I. Prior to deconjugation, the above aqueous layers were examined by systems II and III, which are more suitable for the water-soluble metabolites.

The aqueous layers from step B were combined with the material which was left as residues in the cones in step A. The residues in the cones were extracted in dilute sodium hydroxide and separated from the cell debris by centrifugation (2500 rpm), and the biopolymers were precipitated from the extract with excess ethanol. The precipitated polymers, mostly protein, were lyophilized and dissolved in 0.05M Tris-HCl and were fractionated on Superfine Sephacryl S-200 and the molecular weights of the major fractions were approximated. The major parts of radioactivity were confined to high molecular weight proteins with molecular weights above 67000. The amount of the tissue-bound material was estimated from the pellets in the above centrifugation (2500 rpm). The percentages were calculated on the basis of the total radioactive materials recovered. In most cases, it was over 90%.

Preparation of Microsomes

Adult male Sprague-Dawley rats (6–8 weeks old) were treated ip with phenobarbital (80 mg/kg) dissolved in 0.9% sodium chloride solution once a day for 3 days; they were killed 7 days later by decapitation after a fast for 18 hr. The livers were immediately perfused with 1.15% potassium chloride solution from the inferior vena cava to the portal vein and were excised to prepare 25% homogenates in 1.15% KCl solution with the use of a Potter-Elvenhjem homogenizer and a Teflon pestle. Liver homogenate from the supernatant of 9000 g (20 min) was recentrifuged at 190000 g for 1 hr, and the pellets containing the microsomes and the 190000 g supernatant were stored at $-70°$ C. until used. Protein concentrations were determined by following the methods of Lowry et al, J. Biol. Chem., 193, 265 (1951), with use of bovine serum albumin as the standard. Protein concentrations in microsomes averaged 29.9 mg/mL and in the supernatant 20.8 mg/mL. A portion of the mitochondria-free homogenate was similarly preserved; protein concentration of this fraction w as 11.3 mg/mL.

Metabolism of AMD-OZL 9a and "Reverse" Analogues by Rat Liver Microsomes

The incubation mixture consisted of 500 µg of microsomal protein 1.6 mM NADP+, 16 mM glucose 6-phosphate, 10.1 U of glucose-6-phosphate dehydrogenase, 12 mM $MgCl_2$, 10 mM sodium phosphate-potassium phosphate (pH 7.4) and 0.4–0.8 mM of tritiated drugs (including AMD) in a final volume of 5.0 mL. The mixtures were incubated at 37° C. for 6 hr, after which the reaction was stopped by chilling at 0° C. The chilled mixtures were filtered by centrifugation in tubes containing centriflow membrane cones (Amicon, 1053, molecular weight cut-off 25000). The filtrates were adjusted to pH 5.0 before extraction with water-saturated ethyl acetate (step A).

Equal aliquots of the aqueous layer (step A) were treated either with equal volumes of glucarase (5 mg/mL) in 0.05M acetate buffer, pH 5.0, overnight at 37° C. under nitrogen in a shaking water bath or with buffer alone (step B). The aqueous fractions from step B were mixed with an extract of the Amicon cone-retained material. The metabolites at each step were separated by HPLC (Table II). For extraction of the high molecular weight protein conjugates and other tissue-associated materials, the cones were soaked in 0.1N NaOH solution overnight at 0° C. and were processed as in the preceding section before gel filtration. A Sephacryl S-200 superfine column, 1.0× 60 cm, was made in 6M guanidine hydrochloride, pH 5.0, and the lyophilized material in minimum water, pH 7.0, was added to the top of the column and eluted overnight with 6M guanidine hydrochloride, pH 5.0, at a flow rate of 2 cm/hr. A 2% solution of blue dextran 2000 (100 µL, Pharmacia) was added to the column for calibration. Fractions were collected, and the distribution of the material in the fractions was determined by liquid scintillation counting. Over 90% of radioactivity was found to be eluted immediately after the void volume and along with blue dextran, indicating that almost all the radioactive material was conjugated with a high molecular protein fraction ($\sim$67000). For assay of metabolites, a Varian Moden 5020 gradient liquid chromatograph equipped with a CD-111L chromatography data system was used. The chromatograph was fitted with a Varian reversed-phase $C_{18}$ (octadecylsilane, average column particle size 10 µm) column (0.39×30 cm); a 0.39×2.0 cm precolumn containing ODS Sil-X-1 (average particle size 13 µm) was used as a guard column. The solvent system used was $CH_3CN$-5 mM $NH_4OAc$ buffer, pH 6.4 (62–38, v/v), at a flow rate 1.5 mL/min (system I was used isocratically for organic solvent soluble materials). Two other water-methanol gradient solvents (65–95% water-methanol, 60 min, 1 mL/min, system II; 10–90% water-methanol, 120 min, 1 mL/min, system III, in concave gradient modes) were used mainly for the separation of water-soluble metabolites. The peaks in the chromatograms were monitored by dual detectors, one at a fixed 254 nm and the other at 440, 470, 520 nm, with a variable wavelength detector. The fractions were also collected in a fraction collector every 0.5 min and were quantitated by specific activity. The sensitivity of the assay was 1–10 pmol for the drugs and metabolites. All peaks of the known analogues were confirmed by cochromatography with authentic material. The specific activity of the agents used for metabolic studies was 0.5 Ci/mmol.

Enzymatic Activation of AMD and Analogues (Stimulation of Superoxide Generation)

In these experiments, rat liver microsomes that were prepared as mentioned above were used.

(a) Adrenochrome Formation. The adrenochrome assay of $O_2^-$ was performed in Gilford 250 spectrophotometer equipped with base-line reference compensator (6064) and a cell programmer, auto four cell programmer, and thermostated cell holder 2577. A solution of epinephrine (30 µL, 0.01N HCl) and the microsomes (300 µg) were added to both cuvettes maintained at 37° C. One minute later, NADPH (0.4 mM) was added to the sample side only; the absorbance at the sample side was monitored. The rate of adrenochrome formation was measured at wavelength 480 nm ($\epsilon$4.02 $mM^{-1}$ $cm^{-1}$). Drug solutions were freshly prepared in 150 mM KCl-50 mM Tris at pH 7.4. The drug-dependent percent stimulation of adrenochrome formation are given in Table IV. In the above assays, no more than 100 μM drug solutions were used in order to avoid complication from the high absorbance of the analogues or the metabolites at 480 nm.

(b) NADPH Oxidation. NADPH oxidation, a function of NADPH cytochrome P-450 reductase, was detected by using the above spectrophotometer. Microsomes were added to both cuvettes as in the previous experiment (but epinephrine was not added). NADPH (0.4 mM) was added to the sample side only. Percent NADPH oxidation was calculated in the following manner by monitoring the absorbance at 340 nm: percent NADPH oxidation was equal to $(1 - A_{340}/A'_{340}) \times 100$, where $A_{340}$ is the absorbance at 340 nm of the experimental cuvette and $A'_{340}$ is the absorbance at 340 nm of control cuvette not activated by microsomes. Drug solutions were made as before. The results of this assay are shown in Table IV.

I claim:

1. The compound having the formula:

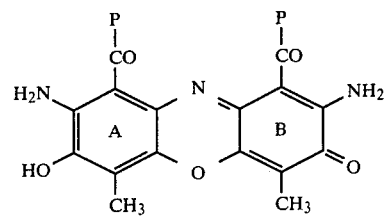

wherein P = Thr—D-Val—Pro—Sar—MeVal
               └——————O——————┘

2. The compound having the formula:

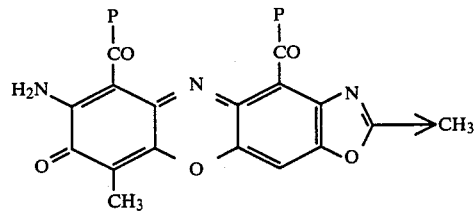

wherein P = Thr—D-Val—Pro—Sar—MeVal
               └——————O——————┘

* * * * *